US00PP19862P2

(12) United States Plant Patent
Michalik

(10) Patent No.: US PP19,862 P2
(45) Date of Patent: Mar. 31, 2009

(54) ***GERANIUM* PLANT NAMED 'PACCRIO'**

(50) Latin Name: *Pelargonium crispum*
Varietal Denomination: Paccrio

(75) Inventor: Andrea Michalik, Dresden (DE)

(73) Assignee: Elsner PAC Jungpflanzen, Dresden (DE)

( * ) Notice: Subject to any disclaimer, the term of this patent is extended or adjusted under 35 U.S.C. 154(b) by 0 days.

(21) Appl. No.: 11/731,878

(22) Filed: Mar. 30, 2007

(51) Int. Cl.
*A01H 5/00* (2006.01)

(52) U.S. Cl. ..... Plt./324
(58) Field of Classification Search ..... Plt./328
See application file for complete search history.

(56) References Cited

PUBLICATIONS

UPOV–ROM GTITM, Plant Variety Database, Apr. 2007, GTI Jouve Retrieval Software, citation for 'Paccrio'.*

* cited by examiner

*Primary Examiner*—Annette H Para
*Assistant Examiner*—S. B. McCormick-Ewoldt
(74) *Attorney, Agent, or Firm*—C. A. Whealy

(57) ABSTRACT

A new and distinct cultivar of Scented *Geranium* plant named 'Paccrio', characterized by its upright and mounded plant habit; freely branching habit; moderately vigorous growth habit; freely flowering habit; single pink-colored flowers with a red purple-colored blotch on the upper petals; and good garden performance.

1 Drawing Sheet

Botanical designation: *Pelargonium crispum*.
Cultivar denomination: 'Paccrio'.

BACKGROUND OF THE INVENTION

The present invention relates to a new and distinct cultivar of Scented *Geranium*, botanically known as *Pelargonium crispum,* and hereinafter referred to by the name 'Paccrio'.

The new Scented *Geranium* is a product of a planned breeding program conducted by the Inventor in Dresden, Germany. The objective of the breeding program is to create new Scented *Geranium* cultivars with attractive flower coloration.

The new Scented *Geranium* originated from a cross-pollination made by the Inventor in Dresden, Germany during the summer of 2002 of two unnamed proprietary selections of *Pelargonium crispum,* not patented. The cultivar Paccrio was discovered and selected by the Inventor as a flowering plant from within the progeny of the stated cross-pollination in a controlled environment in Dresden, Germany in April, 2003.

Asexual reproduction of the new Scented *Geranium* by vegetative terminal cuttings in a controlled environment in Dresden, Germany since October, 2003, has shown that the unique features of this new Scented *Geranium* are stable and reproduced true to type in successive generations.

SUMMARY OF THE INVENTION

The cultivar Paccrio has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Paccrio'.

These characteristics in combination distinguish 'Paccrio' as a new and distinct cultivar of Scented *Geranium* :

1. Upright and mounded plant habit.
2. Freely branching habit.
3. Moderately vigorous growth habit.
4. Freely flowering habit.
5. Single pink-colored flowers with a red purple-colored blotch on the upper petals.
6. Good garden performance.

Plants of the new Scented *Geranium* differ primarily from plants of the parent selections in plant vigor and flower color.

Plants of the new Scented *Geranium* can be compared to plants of the *Pelargonium crispum* cultivar Pacburg, disclosed in U.S. Plant Pat. No. 14,862. In side-by-side comparisons conducted in Dresden, Germany, plants of the new Scented *Geranium* differed from plants of the cultivar Pacburg in the following characteristics:

1. Plants of the new Scented *Geranium* were larger and had longer internodes than plants of the cultivar Pacburg.
2. Leaves of plants of the new Scented *Geranium* were more deeply lobed than leaves of plants of the cultivar Pacburg.
3. Plants of the new Scented *Geranium* had more and larger flower umbels than plants of the cultivar Pacburg.
4. Plants of the new Scented *Geranium* had smaller flowers than plants of the cultivar Pacburg.
5. Plants of the new Scented *Geranium* and the cultivar Pacburg differed in flower color.
6. Plants of the new Scented *Geranium* had longer pedicels than plants of the cultivar Pacburg.

BRIEF DESCRIPTION OF THE PHOTOGRAPH

The accompanying colored photograph illustrates the overall appearance of the new Scented *Geranium*, showing the colors as true as it is reasonably possible to obtain in colored reproductions of this type. Colors in the photograph may differ slightly from the color values cited in the detailed botanical description which accurately describe the colors of the new Scented *Geranium* . The photograph comprises a side perspective view of a typical flowering plant of 'Paccrio' grown in a container.

DETAILED BOTANICAL DESCRIPTION

The aforementioned photograph and following observations, measurements and values describe plants grown in Dresden, Germany in a glass-covered greenhouse during the autumn and winter and under conditions which closely approximate commercial *Geranium* production. During the production of the plants, day temperatures averaged 18° C., night temperatures averaged 16° C. and light levels ranged from 15 kilolux to 100 kilolux. Plants were pinched twice and about five months old when the photograph and the description were taken. In the detailed description, color references are made to The Royal Horticultural Society Colour Chart, 1995 Edition, except where general terms of ordinary dictionary significance are used.

Botanical classification: *Pelargonium crispum* cultivar Paccrio.

Parentage:

*Female, or seed, parent.*—Unnamed proprietary selection of *Pelargonium crispum,* not patented.

*Male or pollen parent.*—Unnamed proprietary selection of *Pelargonium crispum,* not patented.

Propagation:

*Type.*—By vegetative terminal cuttings.

*Time to initiate roots.*—About three weeks at temperatures of 20° C.

*Time to produce a rooted young plant.*—About four weeks at temperatures of 20° C.

*Root description.*—Medium in thickness, fibrous; white in color.

*Rooting habit.*—Freely branching; moderately dense.

Plant description:

*Plant/growth habit.*—Upright to mounded plant habit; densely foliated. Moderately vigorous growth habit. Freely basal branching habit with about ten lateral branches developing per plant.

*Plant height, to top of umbels.*—About 40 cm.

*Plant height, to top of leaves.*—About 30 cm.

*Plant width.*—About 35 cm.

*Lateral branches.*—Length: About 5 cm to 20 cm. Diameter: About 3 mm. Internode length: About 3 cm to 4 cm. Texture: Pubescent. Color: 144A.

Foliage description:

*Arrangement.*—Alternate and opposite; simple.

*Length.*—About 2 cm to 2.5 cm.

*Width.*—About 3 cm to 4 cm.

*Shape.*—Palmately-lobed.

*Apex.*—Rounded to acute.

*Base.*—Cordate.

*Margin.*—Serrate.

*Venation pattern.*—Palmate.

*Fragrance.*—Present; typical of Scented *Geraniums*.

*Texture, upper surface.*—Smooth, glabrous.

*Texture, lower surface.*—Slightly pubescent.

*Color.*—Developing and fully expanded foliage, upper surface: 137A; venation, 137A. Developing and fully expanded foliage, lower surface: 138B; venation, 138B. Zonation pattern: Not observed. Petiole: Length: About 3 cm to 5 cm. Diameter: About 1 mm. Texture, upper and lower surfaces: Smooth. Color, upper and lower surfaces: 146A.

Flower description:

*Flower arrangement.*—Single rotate flowers arranged in loose open umbels arising from apical leaf axils. Umbels displayed above the foliage on strong peduncles. Flowers face upright to outward. Flowers not persistent. Flowers not fragrant.

*Quantity of flowers.*—Freely flowering habit; about five flowers per umbel and about ten umbels per plant.

*Flowering season.*—Year-round under greenhouse conditions. In the garden in Dresden, Germany, flowering is continuous from April until frost in autumn.

*Flower longevity.*—Individual flowers last about six to ten days on the plant; umbels last about three to four weeks on the plant.

*Umbel height.*—About 3.5 cm.

*Umbel diameter.*—About 7 cm.

*Flower diameter.*—About 2 cm.

*Flower depth* (*height*).—About 1.5 cm.

*Flower buds.*—Length: About 7 mm. Diameter: About 3 mm. Shape: Elliptic. Color: 143A.

*Petals.*—Quantity per flower: About five. Length: About 1.7 cm to 2 cm. Width: About 0.8 cm to 1.3 cm. Shape: Round to oval. Apex: Rounded. Base: Attenuate. Margin: Entire. Texture, upper and lower surfaces: Smooth, glabrous. Color: When opening and fully opened, upper surface: More orange than 52C; blotch on upper petals, 59A; color becoming closer to 49A with development; towards the base, close to 155D; venation, 59C. When opening and fully opened, lower surface: 49A; towards the base, close to 154D; venation, 59C.

*Sepals.*—Quantity per flower: Five, arranged in a single whorl. Length: About 7 mm. Width: About 7 mm. Shape: Elliptic. Apex: Acute. Margin: Entire. Texture, upper and lower surfaces: Pubescent. Color, upper and lower surfaces: 143A.

*Peduncle* (*umbel stem*).—Length: About 5 cm to 10 cm. Diameter: About 2 mm. Strength: Strong. Angle: Mostly erect to slightly outward. Texture: Pubescent. Color: 143A.

*Pedicel* (*individual flower stem*).—Length: About 2 cm. Diameter: About 1 mm. Strength: Strong. Texture: Pubescent. Color: 143B.

*Reproductive organs.*—Androecium: Stamen quantity per flower: About five. Anther length: About 2 mm. Anther shape: Oblong. Anther color: 65D. Pollen amount: Moderate. Pollen color: 164A. Gynoecium: Pistil quantity per flower: One. Pistil length: About 1 cm. Stigma shape: Five-parted. Stigma color: 59A. Style length: About 4 mm. Style color: 70B. Ovary color: Close to 144A.

*Seed/fruit.*—Seed and fruit development have not been observed.

Disease/pest resistance: Plants of the new Scented *Geranium* have not been observed to be resistant to pathogens and pests common to Scented *Geraniums* .

Garden performance: Plants of the new Scented *Geranium* have been observed to tolerate rain, wind and temperatures ranging from about 1° C. to about 32° C. and have demonstrated good garden performance.

It is claimed:

1. A new and distinct Scented *Geranium* plant named 'Paccrio' as illustrated and described.

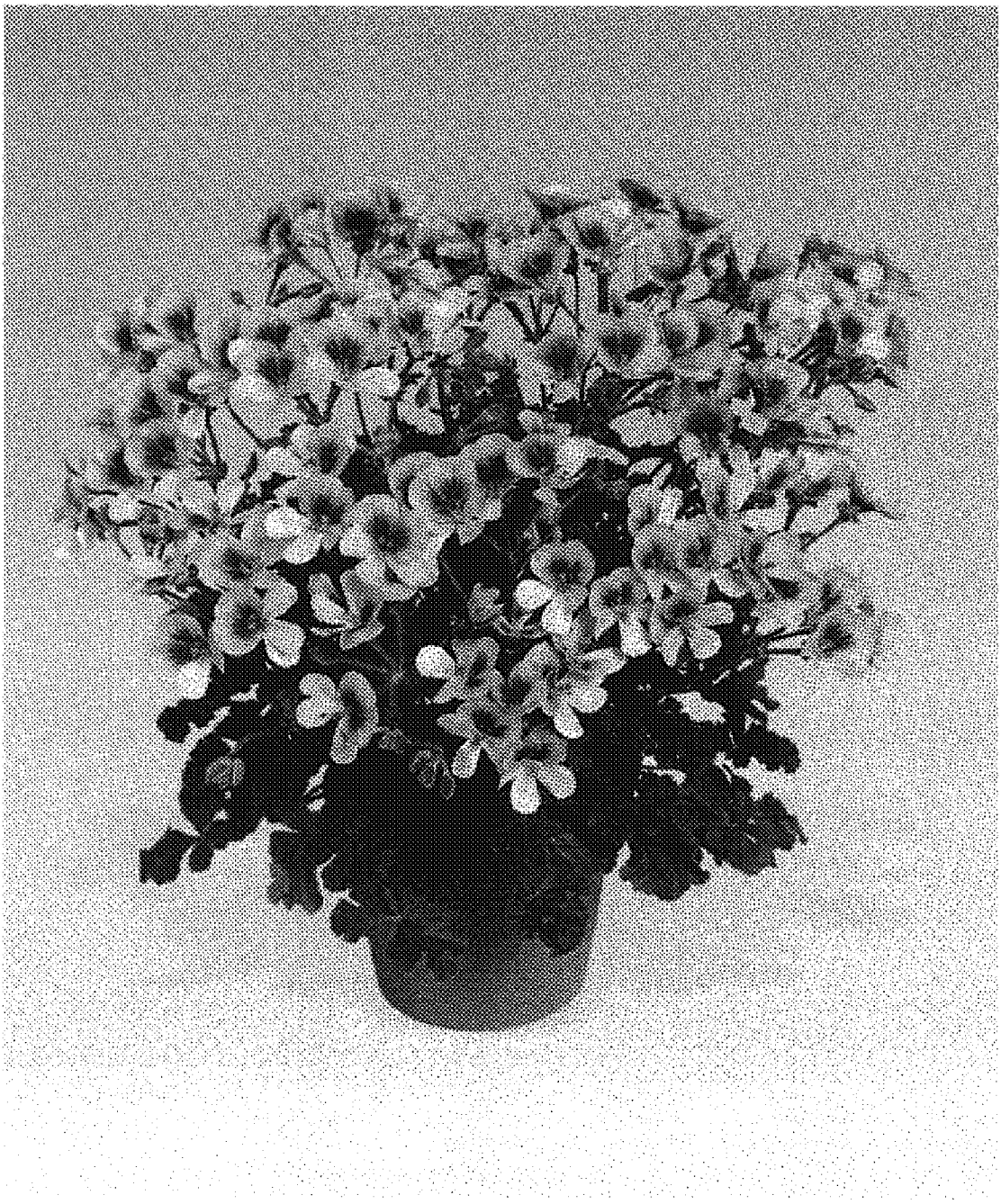

* * * * *